United States Patent
McLaughlin et al.

(10) Patent No.: US 9,516,766 B2
(45) Date of Patent: Dec. 6, 2016

(54) PORTABLE ELECTRONIC DEVICE ASSEMBLY HAVING STERILIZABLE HOUSING

(75) Inventors: Terrance Jon McLaughlin, Naples, FL (US); Edwin Floyd, Bonita Springs, FL (US)

(73) Assignee: ARTHREX, INC., Naples, FL (US)

( * ) Notice: Subject to any disclaimer, the term of this patent is extended or adjusted under 35 U.S.C. 154(b) by 989 days.

(21) Appl. No.: 12/603,595

(22) Filed: Oct. 22, 2009

(65) Prior Publication Data

US 2010/0096963 A1 Apr. 22, 2010

Related U.S. Application Data (60) Provisional application No. 61/107,413, filed on Oct. 22, 2008.

(51) Int. Cl.

| | |
|---|---|
| *A61L 2/08* | (2006.01) |
| *H05K 5/00* | (2006.01) |
| *G06F 1/16* | (2006.01) |
| *H05K 5/02* | (2006.01) |
| *H05K 5/06* | (2006.01) |

(52) U.S. Cl.
CPC .............. *H05K 5/0017* (2013.01); *A61B 46/10* (2016.02); *G06F 1/1626* (2013.01); *H05K 5/0217* (2013.01); *H05K 5/061* (2013.01); *G06F 2200/1633* (2013.01)

(58) Field of Classification Search
USPC ......................................... 312/223.1; 422/26
See application file for complete search history.

(56) References Cited

U.S. PATENT DOCUMENTS

| | | | |
|---|---|---|---|
| 5,562,621 A | 10/1996 | Claude et al. | |
| 5,873,814 A | 2/1999 | Adair | |
| 5,959,557 A | 9/1999 | Lim | |
| 6,132,367 A * | 10/2000 | Adair | 600/101 |
| 7,331,462 B2 * | 2/2008 | Steppe | 206/570 |
| 8,251,891 B2 * | 8/2012 | Moskowitz et al. | 600/104 |
| 2003/0095374 A1 | 5/2003 | Richardson | |
| 2006/0187192 A1 * | 8/2006 | Kagermeier et al. | 345/156 |
| 2006/0274493 A1 * | 12/2006 | Richardson et al. | 361/683 |
| 2007/0095699 A1 * | 5/2007 | Frieze et al. | 206/438 |
| 2007/0119741 A1 | 5/2007 | Wenger et al. | |
| 2007/0202004 A1 * | 8/2007 | Martel et al. | 422/3 |

OTHER PUBLICATIONS

European Search Report for Application No. EP 09 01 3297 completed Feb. 22, 2010.

* cited by examiner

*Primary Examiner* — Kevin Joyner
(74) *Attorney, Agent, or Firm* — Carlson, Gaskey & Olds (57) ABSTRACT

A sterilizable housing for a personal electronic device includes a base, a cover and a user interface. The base is configured for receiving the personal electronic device. The cover is selectively engageable to the base. Both the base and the cover are sterilizable. The user interface provides selective access to the personal electronic device, and is at least partially contiguous with a corresponding user interface of the personal electronic device.

15 Claims, 6 Drawing Sheets

PORTABLE ELECTRONIC DEVICE ASSEMBLY HAVING STERILIZABLE HOUSING

CROSS REFERENCE TO RELATED APPLICATIONS

This application claims priority to U.S. Provisional Application No. 61/107,413, filed Oct. 22, 2008.

BACKGROUND OF THE DISCLOSURE

This disclosure relates generally to a sterilizable housing for a portable electronic device assembly.

A surgical operating room must provide a relatively germ-free environment to ensure the safety of a patient. Accordingly, great care is taken not to compromise the sterility barrier of this environment. Instruments are sterilized, surgeons and nurses are scrubbed-in, and unsterilized objects are left out of the surgical operating room.

From time to time, a surgeon may require access to a personal electronic device in the surgical operating room. For example, the surgeon may wish to use such a device to download and review surgical techniques, communicate with other surgeons located outside of the sterile environment, or conduct other tasks that improve the surgeon's ability to perform surgery. In addition, the surgeon may wish to listen to music in the operating room from another device, such as an MP3 player.

Typically, these personal electronic devices are not manufactured from sterilizable materials. The devices include housings made of unsterile materials or have sensitive components that cannot be subjected to sterilization equipment or procedures. Therefore, a surgeon's preferred personal electronic device is not permitted in the sterile environment of the operating room without a sterile plastic bag around the personal electronic device.

SUMMARY OF THE DISCLOSURE

This disclosure describes an example sterilizable housing for a personal electronic device. The sterilizable housing includes a base, a cover and a user interface. The base is configured for receiving the personal electronic device, and the cover is selectively engageable to the base. Both the base and the cover are sterilizable. The user interface provides selective access to the personal electronic device, and is at least partially contiguous with a corresponding user interface of the personal electronic device.

In one embodiment, a portable electronic device assembly includes a sterilizable housing for a personal electronic device. A housing of the personal electronic device is a separate and distinct component from the sterilizable housing. Moreover, the personal electronic device may be operable to communicate a signal from a sterile environment to a location exterior from the sterile environment.

This disclosure further describes a method for utilizing a non-sterile personal electronic device in a sterile environment. The method includes housing the non-sterile personal electronic device in a sterilizable housing to provide a portable electronic device assembly. The portable electronic device assembly is then positioned within the sterile environment. The portable electronic device assembly is controllable from within the sterile environment to communicate a signal from within the sterile environment to a location outside of the sterile environment.

The various features and advantages of this disclosure will become apparent to those skilled in the art from the following detailed description. The drawings that accompany the detailed description can be briefly described as follows.

DETAILED DESCRIPTION OF THE EXAMPLE EMBODIMENTS

Figure 1:
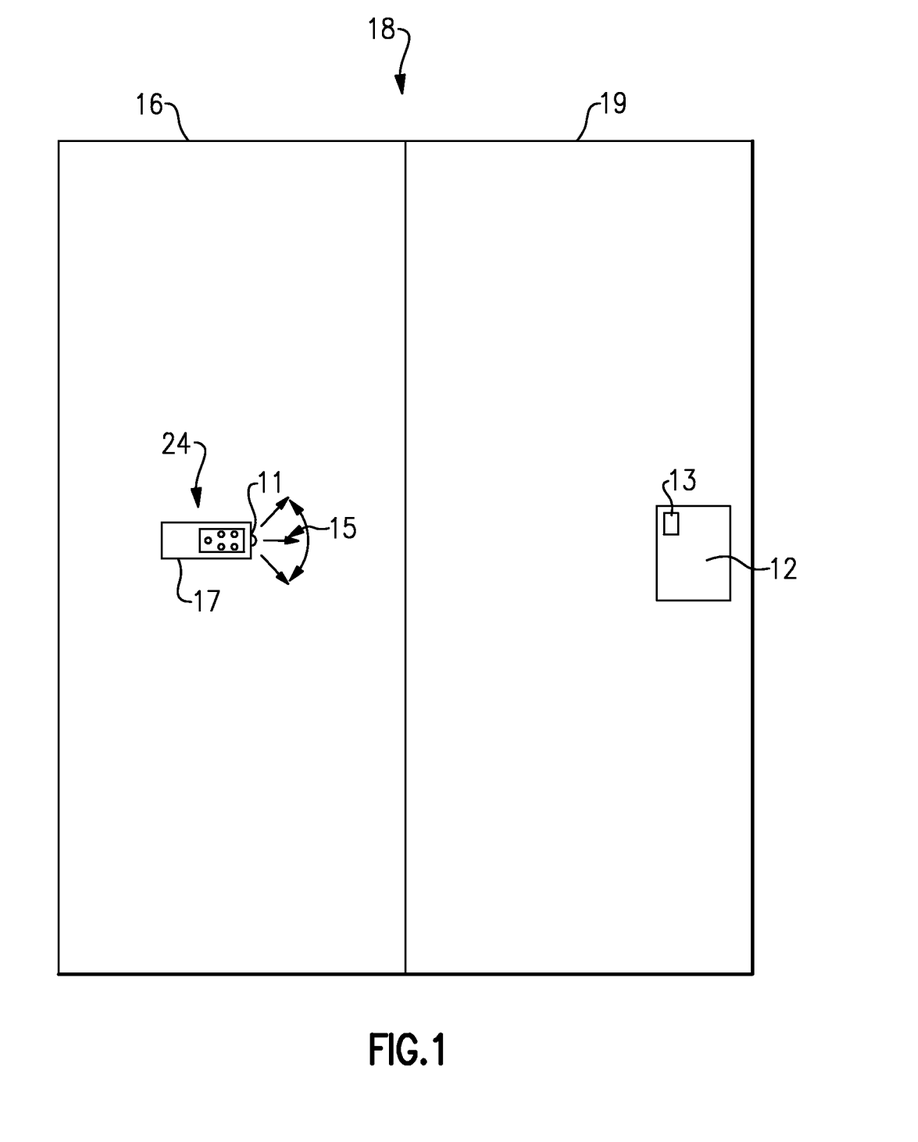
FIG. 1 is a schematic representation of a personal electronic device in a sterile environment.

FIG. 1 illustrates a personal electronic device 24 that is known in the art. The personal electronic device 24 may perform a wide variety of well known functions. For example, the personal electronic device 24 may have a transmitter and a receiver to send and receive communications wirelessly, such as a phone call, text message, or email. The personal electronic device 24 may also include a processor, memory, rechargeable battery and other components housed within a housing 17. In one example, the personal electronic device 24 is a digital device.

The personal electronic device 24 is shown in a sterile environment 16 of a surgical operating room 18 in FIG. 1. The personal electronic device 24 may be configured to play music (such as through an MP3 player or an iPod), to download and view surgical techniques, to communicate with other surgeons located outside of the sterile environment 16, or to perform any other known use.

In this example, the personal electronic device 24 serves as a remote control for a surgeon located within the sterile environment 16 that controls an electronic device 12 located in a non-sterile environment 19 that is outside of the sterile environment 16. The personal electronic device 24 includes an infrared transmitter 11 that communicates with an infrared receiver 13 of the electronic device 12. The control of the electronic device 12 may alternatively be accomplished through non-optical communication, such as by radio signals.

As known, the personal electronic device 24 communicates signals 15 to the electronic device 12 to control the electronic device 12. For example, where the electronic device 12 is a music playing device, such as a stereo, the personal electronic device 24 controls the various functions of the music playing device, including power on/off, volume up/down, track seek up/down and other settings of the electronic device 12.

The aforementioned personal electronic device 24 is a commercially available product and is well known in the art. However, these types of devices are generally not manufactured so as to permit their sterilization for use within a surgical environment. One known method of sterilization is referred to as autoclaving. Autoclaving involves exposing an object to be sterilized to pressurized steam at a specific temperature for a specific amount of time (depending upon the material of the object). One example autoclaving method includes exposing the object to be sterilized to pressurized steam at 275° F. (121° C.) for at least fifteen minutes. Most commercially available personal electronic devices 24 are not designed to withstand the heat and/or moisture that they may be exposed to during sterilization.

Figure 2A:
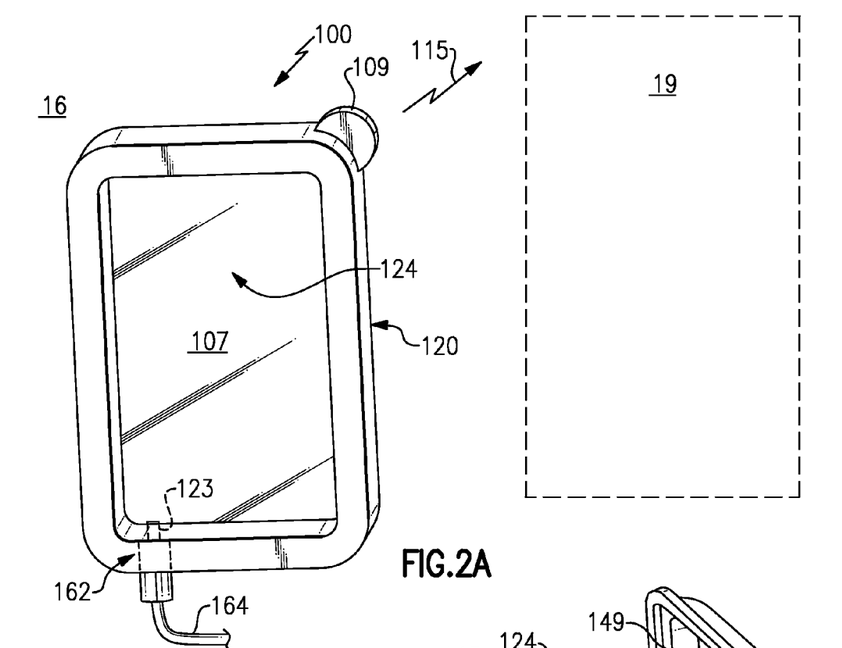
FIG. 2A illustrates a portable electronic device assembly.
Figures 2B, 2C:
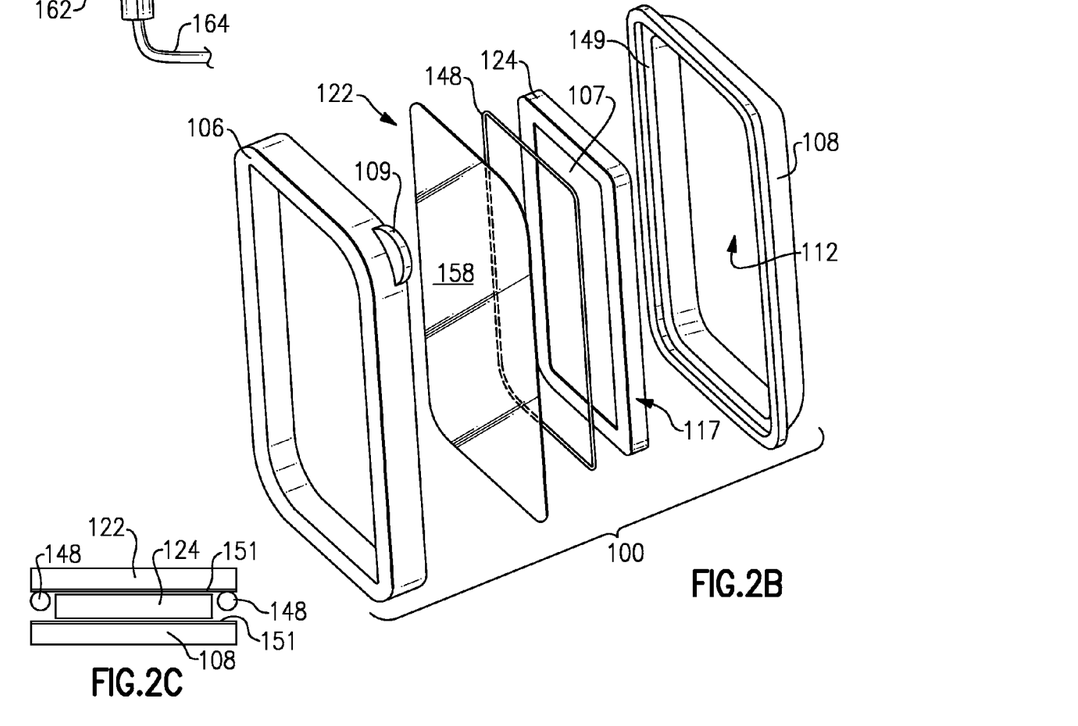
FIG. 2B illustrates an exploded view of the portable electronic device assembly of FIG. 2A.
FIG. 2C illustrates a cross-sectional exploded view of the portable electronic device assembly of FIG. 2A.

FIGS. 2A and 2B illustrate an example portable electronic device assembly 100, which permits the use of a commercially available personal electronic device 124 from within a sterile environment 16. In this disclosure, like reference numerals designate like elements where appropriate, and reference numerals with the addition of 100 or multiples thereof designate modified elements.

The portable electronic device assembly 100 includes a sterilizable housing 120 that houses the personal electronic device 124. The sterilizable housing 120 is made from any sterilizable material. In one example, the sterilizable housing 120 is autoclavable so that it can be used in the sterile environment 16. However, any know sterilization method may be used to sterilize the sterilizable housing 120 of the portable electronic device assembly 100, including, but not limited to, gas sterilization (the use of, for example, ethylene oxide, formaldehyde, hydrogen peroxide, etc.), dry heat sterilization (i.e., the use of disinfectants), radiation, gamma irradiation, and the like.

Once sealed within the sterilizable housing 120, the personal electronic device 124 is operable to communicate wireless signals 115 from the sterile environment 16 to a location 19 that is outside of the sterile environment 16. That is, the non-sterile personal electronic device 124 is permitted within the sterile environment 16 when housed within the sterilizable housing 120, and can be accessed therein to perform a desired task of a user.

In one example, the personal electronic device 124 is a smart device. The smart device is capable of performing a variety of functions, including, but not limited to, communicating with other electronic devices, accessing the internet, playing music, etc. In another example, the personal electronic device 124 includes a cell phone. The personal electronic device 124 includes a user interface 107 having either a touch screen, actuable button, or the like for effectuating tasks, such as making a phone call, for example. The personal electronic device 124 includes a housing 117 that is a separate and distinct component from the sterilizable housing 120. The housing 117 encases the various electronics of the personal electronic device 124, whereas the sterilizable housing 120 provides a sterility barrier to the personal electronic device 124.

In the illustrated example, the sterilizable housing 120 includes a cover 106, a base 108 and a user interface 122 that provides selective access to the personal electronic device 124. The term "selective access" as utilized in this disclosure includes, but is not limited to, viewing, touching, accessing, actuating, controlling, etc. For example, the user interface 122 of the sterilizable housing 120 is here transparent and malleable and permits access to the user interface 107 of the personal electronic device 124 to perform a function, such as viewing a surgical technique, for example.

The sterilizable housing 120 further includes a sterilizable connector 162 for connecting auxiliary components 164, such as headphones, a charger, or the like, to a connector 123 of the personal electronic device 124. The sterilizable connector 162 is aligned with the connector 123 to provide access to the personal electronic device 124.

The sterilizable housing 120 is characterized by any of a variety of designs and configurations. In one example, the cover 106 and the base 108 include similar materials. For example, the cover 106 and the base 108 are constructed of high temperature thermoplastics, thermoplastic elastomers, thermoset elastomers, or other materials having similar properties. In another example, the cover 106 and the base 108 include different materials. For example, the cover 106 includes rubber, and the base 108 includes plastic, or vice-versa. Further examples include a sterilizable housing 120 manufactured from relatively hard materials, relatively soft materials, or a hybrid of both hard and soft materials. In addition, the sterilizable housing 120 can include either a single piece design or a multiple piece design.

A cavity 112 of the base 108 receives the personal electronic device 124. The base 108 and the cover 106 are sterilizable, and are autoclavable, in one example. In addition, the user interface 122 is at least partially sterilizable. For example, the portion of the user interface 122 that is not obstructed by the cover 106 and/or the base 108 is sterilizable. Therefore, once the non-sterile personal electronic device 124 is sealed within the sterilizable housing 120 of the portable electronic device assembly 100, the personal electronic device 124 can be utilized within the sterile environment 16.

The user interface 122 of the portable electronic device assembly 100 includes a protective screen 158 that is disposed between the cover 106 and the personal electronic device 124. The protective screen 158 is at least partially contiguous with the user interface 107 of the personal electronic device 124, and directly contacts the user interface 107, in one example. The protective screen 158 is clear, transparent and/or translucent to enable viewing of the personal electronic device 124, and is at least partially flexible to provide selective access to the user interface 107 of the personal electronic device 124. The protective screen 158 is also sterilizable. In one example, the protective screen is made of polyethylene. Other potential materials for the protective screen 158 include polypropylene, polycarbonate, polymethylpentene, Teflon®, and polymethyl methacrylate.

The user interface 122 of the portable electronic device assembly 100 mirrors the user interface 107 of the personal electronic device 124. For example, the user interface 122 of the portable electronic device assembly 100 and the user interface 107 of the personal electronic device 124 are aligned (i.e., the sizes of the user interfaces 122, 107 are substantially similar) such that a user can selectively access the personal electronic device 124 through the sterilizable housing 120 via the user interface 122.

Figure 3:
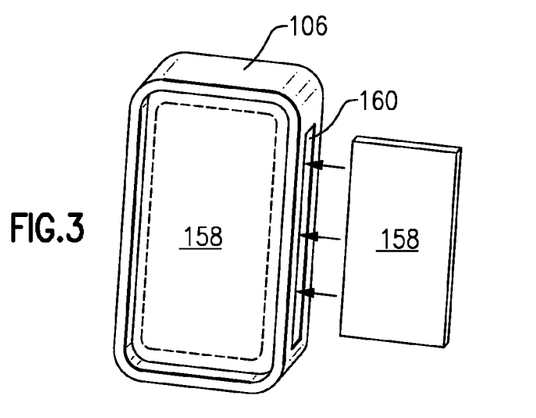
FIG. 3 illustrates a user interface of the portable electronic device assembly of FIGS. 2A and 2B.

In one example, the cover 106 includes a slot 160 that receives the protective screen 158. That is, in this example, the protective screen 158 is removable from the cover 106 (see FIG. 3). The protective screen 158 is selectively removable from the slot 160, such as for single-use applications.

The cover 106 and the base 108 are adjoined to provide a hermetically sealed housing. A first example adjoinment is achieved via a snap-fit connection. The example cover 106 includes a tab 109 that provides a relatively simple mechanism for assembling the cover 106 to the base 108. A sealing member 148 is received between the cover 106 and the base 108 to improve the hermetical seal provided by the sterilizable housing 120 (See FIGS. 2B and 2C). In this example, the sealing member 148 is received on a ledge 149 of the base 108 of the portable electronic device assembly 100. The portable electronic device assembly 100 also includes insulation material 151 (FIG. 2C) that lines the sterilizable housing 120 (at both the cover 106 and the base 108) to further protect the personal electronic device 124 from exposure to heat and moisture.

Figure 4:
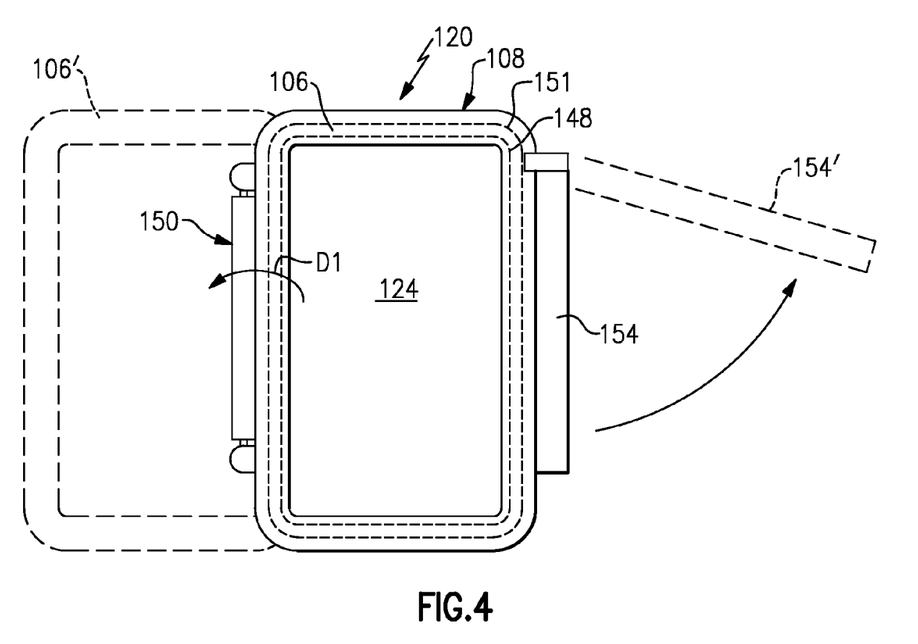
FIG. 4 illustrates additional features of the portable electronic device assembly of FIGS. 2A and 2B.

Another example adjoinment between the base 108 and the cover 106 of the sterilizable housing 120 is achieved with a hinge mechanism 150 (See FIG. 4). The cover 106 is rotatable in a direction D1 relative to the base 108 via the hinge mechanism 150, in this example (open position of cover depicted as 106'). The portable electronic device assembly 100 has a latch arm 154 that selectively locks the cover 106 relative to the base 108 to hermetically seal (in combination with the sealing member 148 and the insulation material 151) the personal electronic device 124 within the sterilizable housing 120 (unlocked latch arm depicted as 154').

Figure 5:
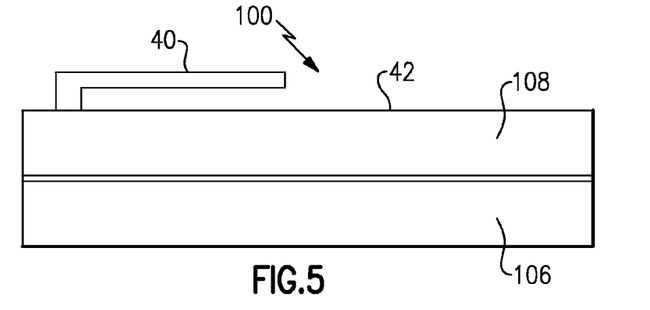
FIG. 5 illustrates a side view of the portable electronic device assembly of FIGS. 2A and 2B.
Figure 6:
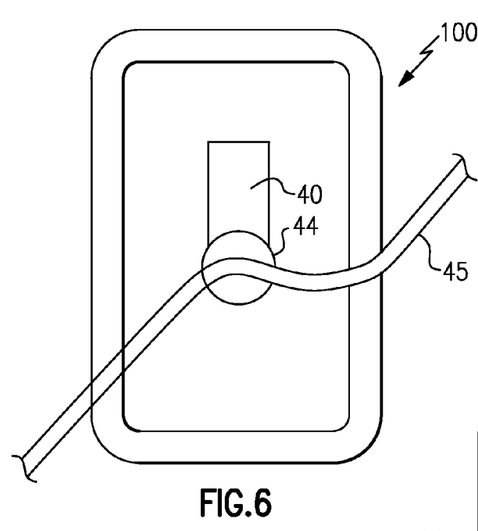
FIG. 6 illustrates a rear view of the portable electronic device assembly of FIGS. 2A and 2B.

FIG. 5 illustrates a clip assembly 40 of the portable electronic device assembly 100. The clip assembly 40 extends from a rear surface 42 of the portable electronic device assembly 100. In this example, the rear surface 42 is disposed on an opposite side of the base 108 from the cavity 112. The portable electronic device assembly 100 is clamped/attached/positioned relative to any surface, such as a surgical drape, with the clip assembly 40. In one example, the clip assembly 40 includes a ring 44 that receives a portion of a surgical drape, cord, chain, string or the like to attach the portable electronic device assembly 100 to a desired article/surface 45 of the sterile environment 16 (See FIG. 6).

Figure 7:
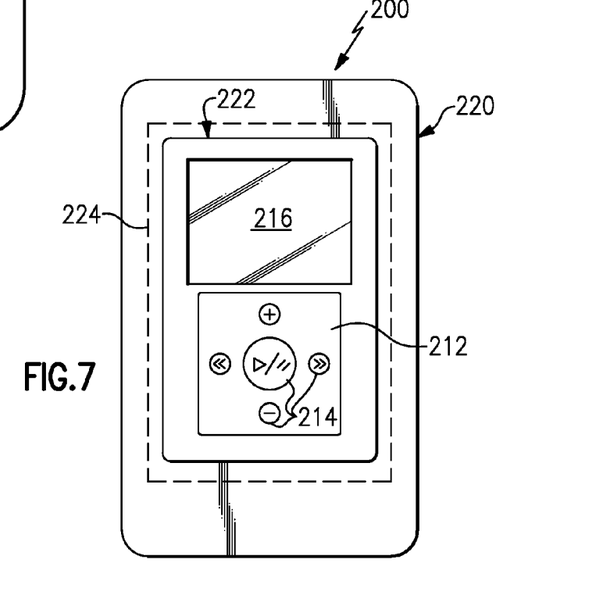
FIG. 7 illustrates another example portable electronic device assembly.

FIG. 7 illustrates another example portable electronic device assembly 200 having a sterilizable housing 220. In this example, the portable electronic device assembly 200 includes a user interface 222 having a control pad 212 that provides selective access to a personal electronic device 224.

The control pad 212 includes one or more actuators 214. Selective manipulation of the actuators 214 is directly transferred to the personal electronic device 224 to control the personal electronic device 224 (see FIG. 8). In this example, the control pad 212 is aligned with the user interface 207 of the personal electronic device 224 such that actuation of an actuator 214 of the control pad 212 in a direction D1 is directly transferred to a corresponding actuator 217 of the user interface 207 of the personal electronic device 224 via a trigger 215. That is, the user interface 222 of the portable electronic device assembly 200 is contiguous with the user interface 207 of the personal electronic device 224 via the trigger 215. In one example, the user interface 222 includes a viewing panel 216 for viewing a portion of the user interface 207 of the personal electronic device 224, although the viewing panel 216 is not a necessary component of the portable electronic device assembly 200.

Figure 8:
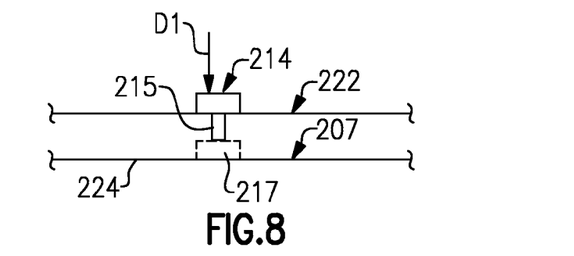
FIG. 8 illustrates a user interface of the portable electronic device assembly of FIG. 7.
Figure 9:
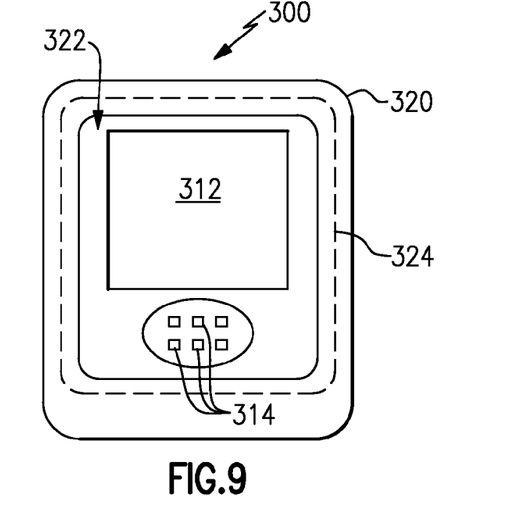
FIG. 9 illustrates yet another example portable electronic device assembly.
Figure 10:
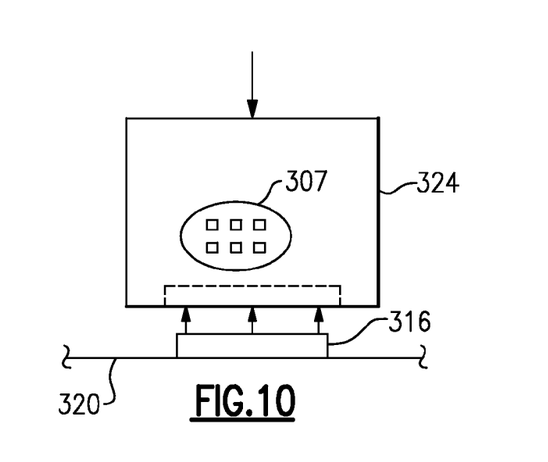
FIG. 10 illustrates selected features of the portable electronic device assembly of FIG. 9.

FIG. 9 illustrates yet another example portable electronic device assembly 300 having a sterilizable housing 320. In this example, a user interface 322 of the portable electronic device assembly 300 includes a viewing panel 312 and a plurality of actuators 314. The viewing panel 312 is used to view a personal electronic device 324, and does not necessarily provide selective access to the personal electronic device 324. A connector 316 (FIG. 10) electrically connects the personal electronic device 324 to the actuators 314 of the user interface 322. Once connected, the actuators 314 control the personal electronic device 324 from the exterior of the portable electronic device assembly 300. For example, the actuators 314 access the user interface 307 of the personal electronic device 324 in much the same way as that described above with respect to the portable electronic device assembly 200 and as depicted in FIG. 8.

Figure 11:
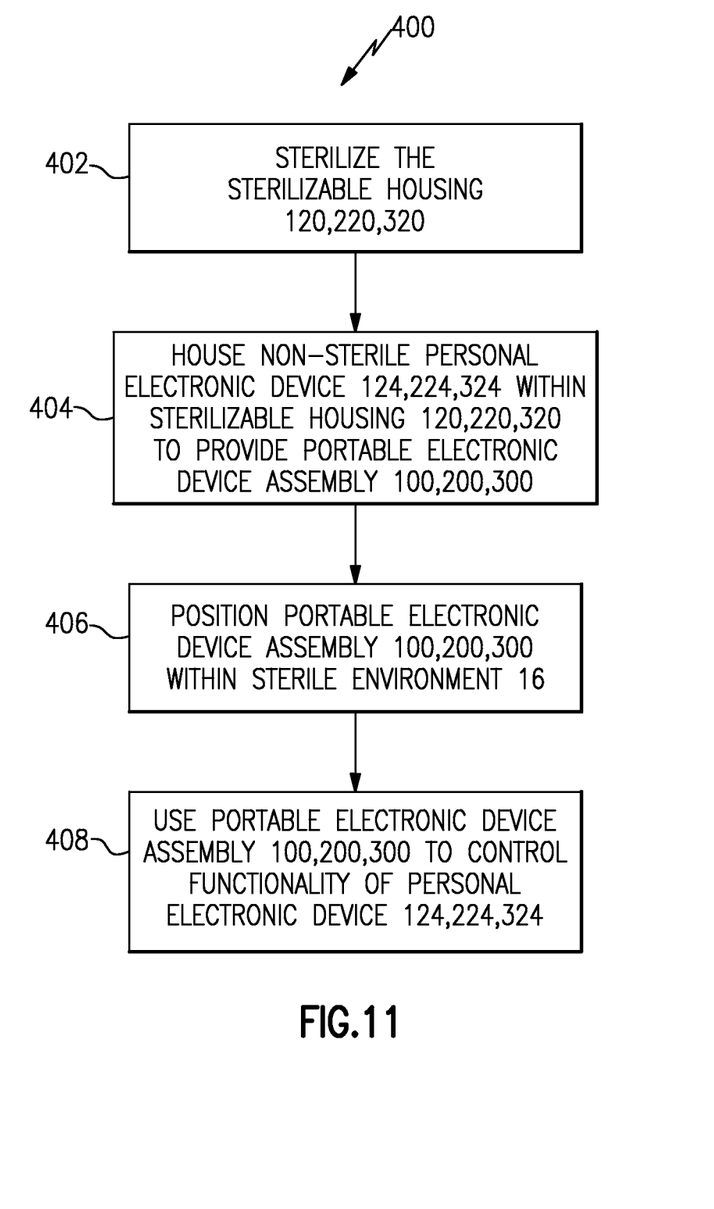
FIG. 11 schematically illustrates a method for utilizing a non-sterile personal electronic device from within a sterile environment.

An example method 400 for utilizing a non-sterile personal electronic device 124, 224, 324 within a sterile environment 16 is schematically depicted by FIG. 11 (with continued reference to FIGS. 1-10). The method begins at step block 402 where the sterilizable housing 120, 220, 320 is sterilized. In one example, the sterilization process includes an autoclaving process. However, other sterilization methods are contemplated as within the scope of this disclosure.

At step block 404, the non-sterile personal electronic device 124, 224, 324 is housed within a sterilizable housing 120, 220, 320 to provide a portable electronic device assembly 100, 200, 300. In one example, the sterilizable housings 120, 220, 320 of the portable digital device assemblies 100, 200, 300 provide a hermetic seal. An aseptic transfer, or other similar sterile transfer method, is used to house the personal electronic device 124, 224, 324 within the sterilized housing 120, 220, 320.

The portable electronic device assembly 100, 200, 300 is positioned within a sterile environment 16 at step block 406. The sterile environment 16 is a surgical operating room, in one example. Finally, at step block 408, the portable electronic device assembly 100, 200, 300 is used to control the personal electronic device 124, 224, 324, such as to communicate wireless signals to a location outside of the sterile environment 16. The user interface 122, 222, 322 of the sterilizable housing 120, 220 and 320 provides selective access to the personal electronic device 124, 224, 324. Because the housing 120, 220, 320 is sterilized, the personal electronic device 124, 224, 324 is accessible from within the sterile environment 16 without compromising the sterility barrier of the sterile environment 16.

In this disclosure, although specific features of the example portable digital device assemblies 100, 200 and 300 are shown in some drawings and not in others, this is for convenience only, as each feature may be combined with any or all of the other features in accordance with this disclosure. In addition, although each example portable electronic device assembly 100, 200, 300 is depicted having a particular size, shape and configuration, this is for illustration only, and a person of ordinary skill in the art having the benefit of this disclosure would understand that the size, shape and configuration of the portable digital device assemblies 100, 200, 300 could change without affecting the overall scope of this disclosure.

Although this disclosure describes portable digital device assemblies used from within a sterile environment of a surgical operating room, it should be understood that other sterile environments could benefit from the example portable digital device assemblies described herein. Moreover, the foregoing description shall be interpreted as illustrative and not in a limiting sense. A worker of ordinary skill in the art having the benefit of this disclosure would recognize that certain modifications would come within the scope of this disclosure. For these reasons, the following claims should be studied to determine the true scope and content of this disclosure.

What is claimed is:

1. A method for utilizing a non-sterile personal electronic device from within a sterile environment, comprising the steps of:
   a) sterilizing a sterilizable housing in an autoclaving process;
   b) housing the non-sterile personal electronic device in the sterilizable housing to provide a portable electronic device assembly;
   c) positioning the portable electronic device assembly within the sterile environment; and
   d) controlling the portable electronic device assembly to communicate a signal from within the sterile environment to a location outside of the sterile environment, wherein said step d) includes downloading a surgical technique onto the portable electronic device assembly.

2. The method as recited in claim 1, wherein the step of sterilizing occurs prior to positioning the portable electronic device assembly within the sterile environment.

3. The method as recited in claim 1, wherein the sterilizable housing includes a base, a cover and a user interface, and the user interface provides selective access to the non-sterile personal electronic device.

4. The method as recited in claim 3, wherein the non-sterile personal electronic device includes a user interface, and the user interface of the sterilizable housing is at least partially contiguous with the user interface of the non-sterile personal electronic device.

5. The method as recited in claim 1, wherein the step of housing is performed using an aseptic transfer.

6. The method as recited in claim 1, wherein the step of housing includes hermetically sealing the non-sterile personal electronic device inside the sterilizable housing.

7. The method as recited in claim 1, wherein the step of controlling includes wirelessly communicating the signal from within the sterile environment to the location outside of the sterile environment.

8. The method as recited in claim 1, wherein the step of controlling includes communicating the signal to a location that is external to the sterilizable housing.

9. The method as recited in claim 1, wherein the autoclaving process includes exposing the sterilizable housing to a pressurized steam at 275° F. (121° C.) for at least fifteen minutes.

10. The method as recited in claim 1, wherein the step of controlling includes wirelessly communicating the signal to communicate with another electronic device that is located outside of the sterile environment.

11. The method as recited in claim 1, wherein the sterile environment is a surgical operating room and the non-sterile personal electronic device is a smart device.

12. The method as recited in claim 11, wherein the smart device is selectively accessible through the sterilizable housing to download and view a surgical technique.

13. The method as recited in claim 11, wherein the smart device is selectively accessible through the sterilizable housing to communicate with other surgeons located outside of the surgical operating room.

14. The method as recited in claim 1, wherein said step a) is performed prior to said step b).

15. The method as recited in claim 1, comprising the step of controlling the portable electronic device assembly to communicate a second signal from within the sterile environment to a location external to the sterilizable housing but still inside of the sterile environment.

* * * * *